US012646248B2

(12) United States Patent
Navab et al.

(10) Patent No.: US 12,646,248 B2
(45) Date of Patent: Jun. 2, 2026

(54) SYSTEM FOR VISUALIZING OCT SIGNALS

(71) Applicant: Carl Zeiss Meditec AG, Jena (DE)

(72) Inventors: Nassir Navab, Munich (DE); Michael Sommersperger, Munich (DE)

(73) Assignee: Carl Zeiss Meditec AG, Jena (DE)

( * ) Notice: Subject to any disclaimer, the term of this patent is extended or adjusted under 35 U.S.C. 154(b) by 215 days.

(21) Appl. No.: 18/532,466

(22) Filed: Dec. 7, 2023

(65) Prior Publication Data

US 2024/0193854 A1 Jun. 13, 2024

(30) Foreign Application Priority Data

Dec. 8, 2022 (DE) .......................... 102022132628.4

(51) Int. Cl.
| | |
|---|---|
| *G06T 15/60* | (2006.01) |
| *G06T 7/10* | (2017.01) |
| *G06T 15/06* | (2011.01) |
| *G06T 15/08* | (2011.01) |
| *G16H 30/40* | (2018.01) |

(52) U.S. Cl.
CPC ................ *G06T 15/60* (2013.01); *G06T 7/10* (2017.01); *G06T 15/06* (2013.01); *G06T 15/08* (2013.01); *G16H 30/40* (2018.01); *G06T 2207/10101* (2013.01)

(58) Field of Classification Search
None
See application file for complete search history.

(56) References Cited

U.S. PATENT DOCUMENTS

2017/0200317 A1* 7/2017 Hannemann ............. A61B 5/00

FOREIGN PATENT DOCUMENTS

| | | |
|---|---|---|
| DE | 102009034994 B3 | 1/2011 |
| DE | 102016200225 A1 | 7/2017 |
| EP | 3005937 A1 | 4/2016 |

OTHER PUBLICATIONS

Kafieh et al., "A Review of Algorithms for Segmentation of Optical Coherence Tomography from Retina", Journal of Medical Signals & Sensors, Oct. 2013, vol. 3, Issue 1, Jan.-Mar. 2013, pp. 45-60.
German Office Action for Application No. 10 2022 132 628.4, mailed Mar. 8, 2023 (19 pages).

(Continued)

*Primary Examiner* — Nurun Flora
(74) *Attorney, Agent, or Firm* — NIXON PEABODY LLP; Jeffrey L. Costellia

(57) ABSTRACT

The present invention relates to a system for visualizing OCT signals, comprising a display means designed for the time-resolved display of image data and a control unit, the control unit being configured to receive a time-resolved OCT signal of a selected field of view of a sample from an OCT system, to ascertain a time-resolved OCT image with a virtual shadow on the basis of the OCT signal, with the virtual shadow being generated in object-specific fashion on at least one area of the OCT image by a virtual irradiation of at least one object of the OCT image by means of a virtual light source, and to control the display means to display the time-resolved OCT image on the display means. The present invention also relates to a corresponding method for visualizing OCT signals.

14 Claims, 7 Drawing Sheets

(56) References Cited

OTHER PUBLICATIONS

Li et al., "A practical comparison between Zhang's and Tsai's calibration approaches," Proceedings of the 29th International Conference on Image and Vision Computing New Zealand, Nov. 2014, pp. 166-171, DOI:10.1145/2683405.2683443.

Ropinski et al., "Efficient Shadows for GPU-based Volume Raycasting," Union Agency—Science Press, Plzen, Czech Republic, Jan. 2008 (8 pages).

* cited by examiner (A)

(B)

SYSTEM FOR VISUALIZING OCT SIGNALS

CROSS-REFERENCE TO RELATED APPLICATIONS

The present application claims priority under 35 U.S.C. § 119 to German Patent Application No. 10 2022 132 628.4, filed Dec. 8, 2022, the contents of which are incorporated by reference herein in their entirety.

SUBJECT MATTER OF THE INVENTION

The present invention relates to a system for visualizing OCT signals, in particular for visualizing time-resolved OCT signals in the form of time-resolved OCT images, containing at least one object-specific shadow. The present invention also relates to a method for correspondingly visualizing OCT signals.

TECHNOLOGICAL BACKGROUND

The use of technological aids is part and parcel of modern medicine. By now, imaging methods and robotic systems are used equally as a matter of course in both surgery and diagnostics. In this context, the use of imaging methods allows the presentation and discrimination of various structures in the patient and the image data obtained from the patient can be used advantageously in diagnostics and also in therapeutic and surgical methods.

By way of example, image data from a patient allows not only a surgeon to plan a surgical procedure better, but also assists them in performing the procedure. Robotic visualization systems are used to assist surgeons when performing surgical procedures. Said systems generally comprise at least one camera for recording images of the region to be operated on, with said camera being carried by a stand with an articulated structure. The stand allows the camera to be positioned relative to the subject by way of translational and/or rotational movements in order to capture images of a desired field of view (FOV) of the region to be operated on. In this context, the use of optical stereo cameras allows the acquisition of 3-D image data.

In addition to the acquisition of pieces of surface information from a desired field of view, for example on the basis of reflected or back-scattered visible light, methods for acquiring pieces of depth information from the field of view have also been developed in the meantime. These methods include optical coherence tomography (OCT), which allows the three-dimensional microscopic imaging of optically transparent and/or reflective objects and hence the recording of volume images of the biological tissue in the observed field of view. Optical coherence tomography (OCT) essentially is an interferometric method using broadband light with a short coherence length. As a rule, systems for acquiring OCT data therefore comprise an interferometer and a broadband light source with a spectral width of more than 1% of the central wavelength.

OCT data can be acquired sequentially or in parallel. By way of example, sequential acquisition of OCT data is implemented by virtue of a low-coherent source light beam being split at a beam splitter into a sample beam and a reference beam which are sent through two arms of an interferometer, with a movable reference mirror being arranged in the reference beam path and the object to be examined being arranged in the object beam path. A path difference between object beam and reference beam, and hence the measured depth, can be set by displacing the reference mirror. The object beam is scanned over the sample in two dimensions by means of a mirror in the object beam path, allowing three-dimensional scanning of the sample as a result.

In the context of such an acquisition of OCT data in the time domain (time domain OCT–TD OCT), the spectral width of the light source $\Delta\lambda$ corresponds to a coherence length $L_C$ of $L_C = \lambda^*/\Delta\lambda$. The axial resolution of an OCT system corresponds to the coherence length $L_C$ of the utilized light and denotes the capability of resolving objects which have a spacing of at least the coherence length along the optical axis. By way of example, a light source in the near infrared range with a central wavelength of 800 nm and a spectral width of 80 nm has a coherence length of 7 $\mu$m and an OCT system having such a source consequently has an axial resolution of approximately 1-10 $\mu$m. The transverse resolution of an OCT system is determined by the optical unit used in the object beam path, in particular by the object lens focusing the light on the object to be examined.

A sequential acquisition of OCT data is also possible in the frequency domain (frequency domain OCT–FD OCT), with a distinction generally being made between the use of a tunable source (swept source OCT) and the use of a dispersive detector (spectral domain OCT–SD OCT). In swept source OCT, the frequency of the excitation light source, for example a laser, is tuned, whereby it is possible to vary a path difference between sample beam and reference beam, and hence the scanned sample depth, even without a displaceable reference mirror. A broadband light source is likewise used in the case of SD OCT, but the detection is preceded by a separation of the frequency components of the interference signal, for example by an optical grating.

Slice and volume data of biological tissue are acquirable by means of OCT, and this can significantly increase the information content for a surgeon. Consequently, an integration of OCT in surgical microscopes is desirable in order to be able to display both video data of the surface of a desired field of view and depth and/or slice images of the field of view, for example in simultaneous and/or overlaid fashion. Since surgeons are predominantly used to working with (in part three-dimensional) video image data to date, the use of overlaid two-dimensional OCT data or OCT images means a change for them. This could overwork the surgeons in the context of OCT image interpretation, and this could possibly even lead to incorrect interpretations, for example if surgeons were to interpret the OCT images just like video image data.

Moreover, OCT images are ascertained from OCT signals by calculation, for example by means of volume rendering, ray tracing, and/or ray marching. These methods inherently offer more varied possibilities for the image generation than the methods or algorithms usually used to generate the (in part three-dimensional) video image data from the image signals acquired by a surgical microscope. Thus, the impetus is to develop methods for generating OCT images (or for visualizing OCT signals) which, from the various possibilities, select those that optimally meet the demands from medical practice.

DE 102016200225 A1 discloses a method for arranging a virtual scene component in a results image depicting a real scene, wherein a 3-D model of the real scene is created on the basis of depth image data from the real scene, this 3-D model is augmented with the virtual scene component (VSB), and the results image is generated by projecting 2-D image data from the real scene on the VSB-augmented 3-D model.

The object of the present invention is therefore that of providing an improved system and an improved method for visualizing OCT signals, which overcome or at least reduce the disadvantages of the prior art and make the correct interpretation of OCT images easier to a surgeon or user.

DESCRIPTION OF THE INVENTION

The object according to the invention is achieved by the subjects of the independent patent claims. Preferred developments are the subject matter of the dependent claims.

A first aspect of the present disclosure relates to a system for visualizing OCT signals, in particular for visualizing such signals acquired by means of a medical device, for example a surgical microscope. In this case, the system according to the invention comprises a display means designed for the time-resolved display of image data. The display means preferably is one or more electronic visual displays, for example at least one electronic visual display of a surgical microscope, an electronic visual display fixedly installed within an operating theater, or a head-mounted display (HMD), for example a pair of video glasses. The electronic visual display is preferably a 4K- and/or 8K-capable electronic visual display and/or a 3-D electronic visual display designed for stereoscopic presentation.

The system according to the present disclosure further comprises a control unit which is connected to the display means, in particular for one-directional or bidirectional data transfer. The control unit is configured to receive a time-resolved OCT signal of a selected field of view of a sample from an OCT system. By way of example, the sample is an operating site on a patient, especially an eye in the case of ophthalmological surgeries. However, the sample may also be any other operating site, for example brain tissue in neurosurgery, tissue located in the ENT region in the case of ENT surgery or the gingiva, tartar or dental nerves in the case of dental surgery. The sample may likewise be any other tissue or preparation (in vivo, in vitro or in situ). The time-resolved OCT signal has preferably been acquired by virtue of a light signal being generated and steered in part as a sample beam to the sample by means of the interferometer and subsequently being superimposed in the interferometer on a reference beam, likewise generated from the light signal, in order to generate an interference pattern.

The control unit of the system according to the present disclosure is further designed to ascertain a time-resolved OCT image with a virtual shadow on the basis of the received time-resolved OCT signal. In this case, the virtual shadow is generated in object-specific fashion by a virtual irradiation of at least one object of the OCT image by means of a virtual light source. In other words, the virtual shadow is generated specifically for a certain object of the OCT image by virtue of this object being irradiated virtually. In this case, the virtual shadow is generated on at least one area of the OCT image, in particular on a specific area of the OCT image. In other words, the invention provides for the determination of both a shadow-generating object and a shadow-receiving area for the generation of the virtual shadow. The virtual shadow generated by the shadow-generating object as a result of the virtual light source is generated on the shadow-receiving area. According to the invention, this renders the generation of semantically segmented shadows possible.

The control unit of the system according to the present disclosure is also configured to display the determined time-resolved OCT image on the display means. In other words, the control unit is configured to control the display means for displaying the time-resolved OCT image with the virtual shadow on the display means. Advantageously, the display is implemented here with the virtual shadow. The virtual shadow facilitates the interpretation of the OCT image here; in particular, it enables a better understanding of distances between objects and areas within the OCT image. The system according to the present disclosure therefore advantageously enables an optimal visualization of the OCT signal in accordance with the needs of the user, whereby the potentials of the OCT signal are optimally exploited, a maximum information content is made available to the user, and incorrect interpretations are avoided.

The control unit is preferably designed to drive an OCT system to acquire a time-resolved OCT signal from a selected field of view (region of interest—ROI) of a sample, with the field of view preferably being selected by a user. Further preferably, the system according to the present disclosure comprises an OCT system. The OCT system preferably comprises a light source, for example a broadband light source, designed to illuminate a sample. This light source preferably is a tunable (swept source) laser, for example a broadband laser, a supercontinuum laser, and/or an ultrashort pulse laser. In this case, a tunable laser at any given time can be a narrowband light source, the central frequency of which however is able to be varied over time in a targeted manner, or formed from a plurality of narrowband light sources. However, any other broadband source can also be used, for example a superluminescent diode, for example in FD-OCT.

Further, the OCT system preferably comprises an interferometer, for example a Michelson, Mach-Zehner, or Koster interferometer, designed for generating and superimposing a sample beam and a reference beam. The interferometer preferably comprises a beam splitter for generating and superimposing the sample beam and reference beam from the light of the broadband source, a reference beam path, and a sample beam path. With further preference, the interferometer comprises means for setting an examined sample depth. Depending on the measurement method, this may be a means for generating a path difference (for instance, a mirror displaceable in the reference beam in the case of SD-OCT), a means for separating light of a specific path difference (for instance, an optical grating in the case of FD-OCT), or means for generating light with a specific path difference (for instance, a tunable source in the case of swept source OCT).

The OCT system further comprises a scanning mechanism designed to scan the sample using the sample beam. In particular, the scanning mechanism is designed to scan the sample beam over the sample in two dimensions. The scanning mechanism preferably is a scanning mirror but other scanning mechanisms may also be used, for example an optical fiber scanner, a prism scanner, a Palmer scanner, or the like. A scanning mechanism is dispensable in the case of an OCT system configured for full-field OCT.

The OCT system further comprises a detector designed to acquire an interference pattern produced by the superposition of sample beam and reference beam. By way of example, the detector is a line detector, a two-dimensional detector array, a photodetector, or a dispersive detector. By way of example, the detector is in the form of a CCD or CMOS detector.

The OCT signal preferably is an interference signal, with the modulation of the envelope of the interference signal encoding reflection properties of the sample. The scanning mechanism allows the sample to be scanned in two dimensions at a sample depth set by way of the path difference. A clock frequency (image refresh rate) for the time-resolved OCT signal arises from the utilized scanning mechanism, the utilized means for selecting or generating the path difference, for example an adjustable mirror in the reference beam, an optical grating upstream of the detector or a tunable broadband light source, and the refresh rate of the detector.

The control unit ascertains a time-resolved OCT image on the basis of the OCT signal by calculation, for example by means of volume rendering, ray tracing, and/or ray marching, with, according to the invention, a virtual shadow of an object being generated by means of a virtual light source. For example, within the scope of ray casting, the position of a potential shadow is ascertained in direct volume rendering by virtue of a shadow ray being emitted in the direction of the virtual light source as soon as the camera ray (i.e., a ray from the observation or viewing direction of the volume rendering) intersects a shadow-receiving area. Here, the shadow ray is emitted from this point of intersection in the direction of the virtual light source, and a shadow is generated on the shadow-receiving area if this shadow ray intersects the shadow-generating object during its derivation. Then, the shadow is generated at the point of intersection of the original camera ray and the shadow-receiving area. A person skilled in the art knows of various methods for calculating shadows within the scope of volume rendering, ray tracing, and/or ray marching, for example the above-described shadow rays, shadow mapping, and deep shadow maps, which may all be used for the purpose of generating the virtual shadow by the control unit of the system according to the present disclosure (cf. for example the publication "Shadow Ray from Ropinski et al., *Efficient Shadows for GPU-based Volume Raycasting*").

According to the present invention, one or more objects of interest are initially identified in part or in full with the aid of a segmentation method. Then, the virtual light source only generates artificial shadows for the objects of interest. Moreover, the shadow-receiving areas are also determined in targeted fashion. By way of example, the virtual light source may cast a virtual shadow of a medical instrument only on the surface of the retina, internal limiting membrane ("ILM") or retinal pigment epithelium (RPE). Consequently, the shadow-receiving area may be a surface layer or an interior layer. Should this be an interior layer, layers thereover are preferably visualized in at least partly transparent fashion. However, a shadow may also be cast without additional segmentation of the shadow-receiving area and in that case relates to all voxels in the OCT volume which are shadowed by the object of interest and are not irradiated by the virtual light source.

Alternatively, the control unit according to the invention is further configured and designed to segment a multiplicity of objects and/or a multiplicity of areas in the OCT signal or OCT image. In other words, there is no targeted segmentation (for example by means of object-specific pieces of information), but all objects and/or areas in the OCT signal or OCT image are initially segmented. The control unit is further designed to ascertain or select the at least one object from the multiplicity of segmented objects on the basis of a user input. The control unit is further designed to ascertain or select the at least one area from the multiplicity of segmented areas on the basis of a user input. Consequently, the virtual shadow may be created only for a single object of interest, for example for a surgical tool, or else for a plurality of objects of interest, for example for a plurality of surgical tools or anatomical structures.

Consequently, an OCT image with at least one virtual shadow is advantageously ascertained by the system according to the present disclosure, with degrees of freedom provided by the OCT system advantageously being exploitable in the generation of the OCT image from the OCT signal. In this case, both the viewing direction of the volume rendering and the position and alignment of the virtual light source are, in principle, independent of an actual viewing direction of a user or an actual light source. Instead, the position and alignment of the virtual light source are specifiable by the user, as described hereinbelow, and/or ascertainable on the basis of device parameters, as described hereinbelow, and serve as a basis for the calculation of the virtual shadow in the OCT image, in addition to the defined (predetermined) shadow-generating object and the defined shadow-receiving (predetermined) area.

According to the invention, the control unit of the system according to the present disclosure is further configured to ascertain the at least one object and/or the at least one area by segmenting the OCT signal or OCT image. In this case, the segmentation is implemented in particular before the generation of the virtual shadow, on the basis of the OCT raw data, and/or on the basis of an OCT image ascertained therefrom. As a result of the segmentation of OCT signal or OCT image, the control unit is advantageously able to identify the position of the at least one object and/or of the at least one area in the OCT volume. A person skilled in the art knows of various algorithms for automatically segmenting objects in image data, and these algorithms are presently used by the control unit in order to ascertain shadow-receiving areas and shadow-generating objects. These algorithms include both conventional threshold value-based image processing algorithms and more recent 2-D and 3-D segmentation networks that are based on machine learning (for example, a U-Net segmentation network). The control unit is preferably designed to obtain the segmentation from individual 2-D OCT B-scans or directly from the entire 3-D OCT volume. The positions obtained in the process are advantageously usable in volume rendering, ray tracing, and/or ray marching, as described hereinabove.

The control unit according to the present disclosure is preferably designed and configured to ascertain or segment the at least one object on the basis of object-specific pieces of information. In other words, additional pieces of information that characterize the object can be used for the identification and segmentation of this object. For example, these pieces of information are pieces of information relating to the size, geometry, estimated relative position and/or material of the object. Likewise preferably, the control unit according to the present disclosure is preferably designed and configured to ascertain the at least one area on the basis of area-specific pieces of information. Thus, additional pieces of information that characterize the area can also be used for the identification and segmentation of this area. For example, these pieces of information are pieces of information relating to the estimated relative position (layer sequence), nature of the surface, and/or type of tissue of the area. The object-specific and/or area-specific pieces of information further preferably also comprise pieces of information relating to a surgical phase (a phase of a specific operative procedure), in which the segmentation of the respective object or the respective area is desired. In combination with an algorithm for identifying the phase, a variable segmentation of objects and/or areas can consequently be implemented fully automatically.

The system according to the present disclosure preferably further comprises an interface designed to acquire a user input. The interface preferably is a hand switch, a foot switch, and/or means for recognizing a head movement and/or eye movement or an actual viewing direction, for example integrated into video glasses or into a head-mounted display, HMD. The interface may further be designed to capture voice commands and may comprise at least one microphone to this end. Likewise preferably, the interface is a keyboard, a joystick, a mouse, a touchscreen, or a combination thereof.

According to this preferred embodiment, the control unit is further designed to control the interface for acquiring the user input. Further preferably, the user input is preceded by a prompt for input, output to the user by means of the output means for example. Likewise preferably, the user input is a selection of a plurality of predefined input options, which for example specify a virtual illumination direction and/or a procedure to be carried out. Likewise preferably, the user input is a user input which is freely definable by the user within a given scope. Likewise preferably, the control unit is designed to assist the user with the user input, for example by displaying a plurality of dialogs for the targeted query of specific user inputs.

In a likewise preferred embodiment of the system according to the present disclosure, the control unit is configured to ascertain the OCT image as a 3-D volume image from the OCT signal by means of volume rendering, ray tracing, and/or ray marching. Particularly preferably, the control unit is configured to ascertain the time-resolved OCT image as a three-dimensional volume image from the perspective of a virtual viewing direction. In addition to the display of OCT images in an "en-face" representation, which is to say in a plan view, the control unit therefore also enables the perspective display of the OCT signals. Likewise preferably, the control unit is further designed to display the OCT signals in the form of slice images in a height direction of the sample (so-called B-scans). The display of the time-resolved OCT images as a perspective three-dimensional volume image from different perspectives advantageously allows the maximum of depth information to be obtained about the object. In particular, both the straight display from the bird's eye view (plan view, "en face"), the latter from different virtual viewing directions (azimuth angle and elevation angle), and also slice images (B-scans) along different cut lines may be advantageous, for example in order to obtain the respectively relevant pieces of information about the sample during different phases of a procedure. According to this embodiment, the control unit is further designed to also ascertain the virtual viewing direction on the basis of a user input, for example by means of a user input specifying an azimuth angle and an elevation angle of the viewing direction.

Further preferably, the control unit is configured to vary the position, alignment, and/or type of the virtual light source. As already mentioned, the rendering of 3-D OCT volume images may lead to problems with regards to the correct interpretation of spatial pose relationships between objects/areas in the OCT image. For example, the relative pose of a surgical tool tip and an anatomical structure may be interpreted incorrectly, depending on the viewing angle. This problem is solved by positioning one or more virtual light sources. In principle, the virtual light source can be any type of light source, for example a punctiform light source, directed (parallel) light, or any other light source. The virtual light source then generates virtual shadows depending on its type, position, and alignment. The positional perception of objects of interest in the OCT image and the estimate of the distance thereof from anatomical structures can be assisted by varying type, position, and/or alignment. Likewise preferably, the control unit is configured to display the position, alignment, and/or type of the virtual light source in the time-resolved OCT image. Advantageously, this additionally assists the understanding of the user of the generated at least one virtual shadow.

According to this embodiment, too, the system according to the present disclosure preferably comprises an interface designed to acquire a user input. The interface preferably is the interface already described above. Then, the control unit is preferably configured to set the position, alignment, and/or type of the virtual light source on the basis of the user input. Thus, the position of the virtual light source can advantageously be set manually in order to vary the size and direction of the virtual shadow. This allows the user to carry out precisely the manipulations that they consider helpful for their personal understanding.

As an alternative or in addition, the system according to the present disclosure further comprises a device interface designed to acquire a device parameter. The device interface is preferably an interface for connecting a surgical-microscopic system, as still described in detail hereinbelow. Likewise preferably, the device interface however is also an interface for connecting any other imaging system. Further, the device interface can be an interface for connecting a medical instrument. Likewise preferably, a system for tracking a medical or medical engineering instrument is connectable via the device interface, wherein the tracking system may also be the surgical-microscopic system or any other imaging system. By way of example, the medical instrument is a pointer, a probe, a pair of tweezers, an awl, a phaco tip, an endoscope, and endo LED of a gripper or the like. According to this embodiment, the control device is preferably configured to communicate, in particular communicate bidirectionally, with the device interface and further configured to drive the device interface to acquire a device parameter of a device connected by means of the interface.

According to this embodiment, the control unit is further designed to ascertain the position, alignment, and/or type of the virtual light source on the basis of a device parameter acquired by means of the device interface. Preferably, the device parameters of a connected surgical-microscopic system or other imaging system can be used to ascertain the position, alignment and/or type of a real light source of the surgical-microscopic system or other imaging system and to equate the position, alignment, and/or type of the virtual light source therewith. For example, this allows an overlaid or simultaneous display of video image data and OCT image data with identical illumination and shadow conditions. Advantageously, the virtual shadow can thus be generated by an artificial light source which corresponds with the real surgical light source in the operating site in terms of its type, position, and/or alignment. The position and alignment of the real light source may also be ascertained by image processing or image analysis in the OCT image or in the surgical-microscopic "en-face" view.

In a likewise preferred embodiment of the system according to the present disclosure, the said system further comprises a medical instrument. Preferably, the device parameter describes a pose, a position, and/or a state of a connected medical (or a tracked medical) instrument or of a medical (or a tracked medical) instrument tracked by means of the tracking system. By way of example, the medical instrument is a probe, a pointer, a pair of tweezers, an awl, a phaco tip, an endoscope, an endo LED or the like.

In this case, a type of the medical instrument can preferably be implemented on the basis of a device interface for connecting the medical instrument, by means of a tracking system (for example by identifying a target ID), and/or on the basis of an input via a user interface. Likewise preferably, a type of the medical instrument introduced into the field of view of the surgical-microscopic system is identified by an image analysis of the video image data, for example by means of segmentation and object recognition. A position of the medical instrument is preferably ascertained on the basis of the detection of a marker and/or a target comprising a plurality of markers, wherein the marker may be a label on or a structure of the medical instrument. The marker and/or the target are preferably detected by means of the surgical-microscopic system and optionally using additional light sources (for example infrared LEDs) and/or following a registration/calibration of the medical instrument (for example by positioning the one tip of the medical instrument at a defined location). The spatial pose of the medical instrument may also be ascertained by the instrument itself. Advantageously, the type, position, and/or alignment of the virtual light source in this embodiment can be set automatically on the basis of the distance of the instrument from the eye anatomy or any other region of interest of the OCT image. By way of example, when the distance between the medical instrument and the shadow-receiving area, for example an anatomical tissue, decreases, the virtual light source can be arranged at a decreasing distance from this area in order to emphasize the distance between the instrument and tissue by way of the shadow.

A state of the medical instrument introduced into the field of view of the surgical-microscopic system is likewise preferably ascertained on the basis of an image analysis of the video image data. By way of example, whether tweezers are opened or closed can be identified on the basis of the image data. Moreover, a user input for changing a state can be read by the control unit; for example, a user input for activating a phaco tip signals a change in the state thereof. Further, a sensor attached to the medical instrument can detect the change in the state of the latter, for example tweezers being closed, and can transmit a corresponding sensor signal to the control unit. A device parameter relating to the state of a connected medical instrument, received via the device interface, preferably also comprises the actuation of an input means of the medical device, with the result that the device parameter in this case also represents a user input at the same time. Likewise preferably, different device parameters are considered together, for instance the pose of the medical instrument (for example ascertained by the instrument itself and/or by a tracking system) and the actuation of an input means of the medical instrument. Thus, for example, a sequence of positions and/or alignments of the virtual light source corresponding to a sequence of poses of the instrument is advantageously settable. A device parameter describing the medical engineering or medical instrument is received via the device interface from the instrument itself or from a tracking system.

According to this preferred embodiment, the control unit is further configured to ascertain the position, alignment, and/or type of the virtual light source on the basis of the position, the type, and/or the state of the medical instrument. Thus, the position, alignment, and/or type of the virtual light source can be ascertained, for example, in a manner corresponding to the pose of a pointer or in a manner corresponding to the state of a gripper. A change in the state of a medical instrument of a specific type and/or at a specific location is preferably indicative of a specific phase of an operation. Consequently, recognizing the position, the type, and/or state of the medical instrument can be used to choose the optimal virtual illumination for this phase. In addition to the setting of the virtual light source, this optionally also comprises an adjustment of further display parameters of the OCT images, for example a zoom level, a virtual viewing direction, a displayed depth, a cut direction, etc.

By way of example, using the aforementioned pieces of information, the control unit is able, either automatically or on the basis of a user input, to ascertain that a performed procedure is membrane peeling by means of tweezers and, in this case, to further ascertain a distance or a position of the tweezers relative to the eye and to adapt or set the type, position, and/or alignment of the virtual light source on the basis of the aforementioned ascertainments. In a further example, the control unit is preferably able, either automatically or on the basis of a user input, to ascertain that a performed procedure is a subretinal injection of a "bleb" or a placement of a retina stent and, on the basis thereof, adapt the type, position, and/or alignment of the virtual light source in such a way that a user is assisted with the positioning of the needle or stent, for example by virtue of the virtual light source being positioned with the smallest possible distance from the retina and the virtual shadow being projected on an area below the retina, with the result that a user is able to make an optimal estimate as to when the needle is placed correctly.

Likewise preferably, the control unit is configured to display the virtual shadow with a color code in the time-resolved OCT image. In other words, the virtual shadow can be visualized in grayscale levels or in color, the latter for example in order to emphasize the synthetic nature of the virtual shadow and in order to be able to distinguish it better from real shadows. In this case, the coloring may be fixedly specified or may likewise be dynamically adapted, for example on the basis of the distance between a medical instrument and an area of interest in an anatomy, for example of an eye. Further, the coloring is preferably set on the basis of a user input or a device parameter.

In a preferred embodiment of the system according to the present disclosure, an OCT signal includes a multiplicity of (first) tuples, which each comprise (or represent) a volume element of the sample and a scattering intensity. In this case, the volume element of the sample is preferably represented by three spatial coordinates (for example x, y and z) and can be interpreted for example as a sample voxel. The tuple may contain further values in addition to the scattering intensity. According to this embodiment, the display means comprises a multiplicity of pixels and the control unit is configured to ascertain the time-resolved OCT images in such a way on the basis of the (first) tuples and on the basis of the resolution of the display means that certain pixels correspond to certain volume elements, which is to say that certain pixels display certain volume elements of the sample. In other words, the control unit ascertains a mapping of pixels of the display means and volume elements of the sample. In this case, this mapping may depend on further settings, for example a scanning resolution of the utilized scanning mechanism, but is preferably constant over time for a given selection of settings such as virtual viewing direction, zoom level, and stereo angle. Therefore, the control unit realizes spatial registration between pixels of the display means and the OCT signals or the ascertained OCT images. The control unit is further configured to ascertain the time-resolved OCT images such that a virtual shadow ascertained on certain volume elements (for example by means of ray tracing, as described above) is displayed on corresponding pixels.

Further preferably, the control unit is configured to locally register, on the basis of acquisition parameters of the OCT system, the OCT signals acquired by the OCT system. In this context, a local registration of these signals denotes correct linking of these signals to a reference coordinate system, for example the coordinate system of the patient during a procedure, and allows unique mapping of coordinates of the patient space on corresponding coordinates of the signal space. A registration of the signals preferably requires a calibration of the OCT system. The acquisition parameters of the OCT system preferably include calibration parameters. The acquisition parameters of the OCT system preferably take account of the scanning mechanism and/or the detector of the OCT system. On the basis of the local registration on the basis of the acquisition parameters, it is advantageously possible to correctly depict structures of the patient situated at defined coordinates of the patient space at the corresponding coordinates in the image space of the OCT images, especially with the correct relative poses with respect to one another.

In a particularly preferred embodiment of the system according to the present disclosure, the said system further comprises a surgical-microscopic system designed to acquire a time-resolved image signal from the selected field of view of the sample. The surgical-microscopic system comprises a real light source and preferably comprises an optical unit, in particular for detecting light from the real light source, reflected or back-scattered from the sample. By way of example, the optical unit comprises an objective lens and an eyepiece; however, it may moreover comprise further components, in particular further lens elements, mirrors, beam splitters, and/or the like. The surgical-microscopic system further comprises an image sensor which is designed to acquire a time-resolved image signal of the selected field of view (region of interest—ROI) of a sample. The optical unit and the image sensor are preferably formed in integrated fashion, for example as parts of a camera of a surgical microscope. According to this embodiment, the control unit is further designed and configured to ascertain video image data corresponding to the acquired time-resolved image signal. In particular, the time-resolved image signal is a multiplicity of signals assigned to surface elements of the sample, which are acquired sequentially or simultaneously for a specific scan of the sample surface, wherein the scan is determined by a scanning mechanism and/or the image sensor. Further, the time-resolved image signal has a clock frequency (image refresh rate), which is determined by a scanning mechanism and/or the image sensor. From this image signal, the control unit generates video image data with a raster (resolution) and an image refresh rate suitable for display on the display means. The control unit is further configured to display the video image data by means of the display means.

In the system according to the present disclosure, an image signal preferably includes a multiplicity of (second) tuples. In this case, each (second) tuple comprises (or represents) a surface element of the sample and at least one grayscale value. In this case, the surface element of the sample is preferably represented by two lateral spatial coordinates (for example x and y) and can be interpreted for example as a sample pixel. In addition to the grayscale value, which ultimately arises from a detected intensity, each (second) tuple may moreover also comprise color values, for example within the scope of the detection of intensities for different colors by means of color filters disposed upstream of the image sensor. According to this embodiment, the control unit is moreover configured to ascertain the video image data in such a way on the basis of the (second) tuples and on the basis of a resolution of the display means that certain pixels display certain surface elements of the sample. In other words, the control unit ascertains a (second) mapping of pixels of the display means and surface elements of the sample, in addition to the (first) mapping of pixels of the display means and volume elements of the sample. In this case, this (second) mapping may depend on further settings, for example a zoom level of the surgical-microscopic system, but is preferably constant over time for given settings. The (second) mapping preferably corresponds to the (first) mapping. Therefore, the control unit also realizes a spatial registration between pixels of the display means and image signals (video image data) of the surgical-microscopic system.

Further preferably, the control unit is moreover configured to locally register, on the basis of acquisition parameters of the surgical-microscopic system, the image signals acquired by the surgical-microscopic system. A registration of the signals preferably requires a calibration of the surgical-microscopic system. The acquisition parameters of the surgical-microscopic system consequently preferably comprise calibration parameters and/or optical settings of the surgical-microscopic system, for example a focal length and/or a zoom level of an optical unit (camera) utilized. Moreover, the acquisition parameters preferably also comprise a set of intrinsic parameters of the surgical-microscopic system. In this case, the intrinsic parameters determine a relationship between the coordinate system of an image signal and the coordinate system of the associated imaging sensor. In this case, the type of the intrinsic parameters depends in particular on the type of imaging sensor utilized, with imaging sensor in this case denoting both the actual sensor and the utilized optical unit. In the case of Tsai's camera calibration, the intrinsic parameters for example comprise an effective focal length, the coordinates of a principal image point (center of the distortion) of an image signal, a first scaling factor, and/or a first radial lens error coefficient (distortion coefficient). As an alternative to the aforementioned intrinsic parameters, other intrinsic parameters can also be used, for example for Zhang's camera calibration (cf., for example, "*A practical comparison between Zhang's and Tsai's calibration approaches*", Li et al., Proceedings of the 29th International Conference on Image and Vision Computing New Zealand, November 2014 Pages 166-171, DOI:10.1145/2683405.2683443).

The local registration of the OCT signals together with the local registration of the image signals advantageously enables the generation and display of the OCT images and the video image data, with the result that the generated time-resolved OCT image corresponds at least to one portion of the displayed video image data. Preferably, an OCT signal is acquired from the entire field of view and an OCT image of at least a part of the field of view is created. Likewise preferably, an OCT signal is acquired from a portion of the field of view and an OCT image of at least a part of the portion of the field of view is created. The control unit is further designed to display the time-resolved OCT image on the display means at the position of the portion of the video image data. Preferably, video image data and an OCT image of the entire field of view are created and are each displayed on the entire display means. Likewise preferably, an OCT image of a portion of the field of view is generated and displayed on the display means at the position of the video data corresponding to this portion of the field of view. In other words, video image data and OCT images corresponding to the same portion of the sample are displayed at the same location of the display means. The system according to the present disclosure consequently enables a seamless integration of video image data and OCT images on the display means, whereby easier viewing of the multimodal image data is enabled for a user. This allows the multimodal image data to be observed without moving the head or the eyes, which has an advantageous effect on the attentiveness of the surgeon, in particular in the case of imaging during operative procedures.

According to this embodiment, the control unit is preferably configured to generate the virtual shadow by means of a virtual light source that corresponds to the real light source of the surgical-microscopic system. Consequently, there advantageously is no deviation between shadows caused by the real light source and the at least one virtual shadow during a simultaneous or sequential display of the video image data and time-resolved OCT image on the display means. Consequently, a distraction or even confusion of a user is avoided, and there can advantageously be a joint display of video image data and OCT images without disadvantages.

The control unit of the system is preferably configured to simultaneously display the video image data and the time-resolved OCT image on the display means. This particularly advantageously allows the simultaneous consideration of both image modalities by a user. To nevertheless allow a distinction to be made between the different image data, the control unit is further preferably configured to display the video image data with a first level of transparency and the time-resolved OCT image with a second level of transparency. In this case, the first and the second level of transparency preferably differ from one another. The first and the second level of transparency likewise preferably vary over time. By way of example, the image signal is initially displayed with a transparency of 0% while the OCT image is displayed with a transparency of 100%. Over the course of time, the transparency of the image signal is then adjusted continuously from 0% to 100% while the transparency of the OCT image is simultaneously adjusted from 100% to 0%. This consequently ensures a continuous transition between the display of the video image and of the OCT image.

In a likewise preferred embodiment of the system according to the present disclosure, the control unit is further designed to locally register the video image data and OCT images by image analysis. In this case, a local registration of these image data denotes correct linking of these images in a common image coordinate system. The registration on the basis of the image data consequently allows relative linking of the image data for a display of the same structures that is as congruent as possible. By way of example, structure or tissue boundaries can be recognized in the video image data and the OCT images by means of image analysis, for example edge detection or the like, and can be compared to one another. These structures can then be overlaid on one another on the display means by way of a translational displacement, rotation, and/or scaling. The local registration of the image data is preferably implemented in addition to a local registration of the acquired signals, as described hereinabove.

In a likewise preferred embodiment of the system according to the present disclosure, the control unit is configured to display the video image data and the time-resolved OCT image sequentially on the display means. In other words, only one of video image data and OCT images is displayed at any one time, at least at a specific location on the display means. This advantageously allows a clear distinction to be made between video image data and OCT data and likewise advantageously allows a simultaneous display of the various image data at different locations on the display means.

Particularly preferably, the control unit is configured to display the video image data and the time-resolved OCT image with the same magnification, the same perspective, and/or the same stereo angle. In the case of a simultaneous display of both video image data at the same location on the display means, this preferably enables a perfect overlay of both image data and may advantageously enable a display with an optimized contrast. In the case of a sequential display, preferably a display with the same magnification, the same perspective, and/or the same stereo angle occurs at the transition between the locally registered image data. Likewise preferably, the virtual shadows are generated in the OCT image, at least at the transition, by means of a virtual light source with the same position, of the same type, and/or with the same alignment as the real light source for the video image data. Consequently, a fluid transition occurs between the display of the image data. Only a display of the surface (top view) is possible in the case of the video image data. For example, this corresponds to an "en face" OCT image. As soon as there has been a transition from video image data to the OCT image, the magnification, perspective, and/or stereo angle is further preferably adaptable in order to advantageously enable an improved view with an optimal depth perception. In particular, there can be a change from the initial "en face" view to a perspective display, for example by way of a continuous transition of the virtual viewing direction, or to a slice view (OCT B-scan), in order to ensure the best view.

According to a further preferred embodiment of the system according to the present disclosure, the display means is preferably designed to display image data stereoscopically. The display means preferably is a display means designed to display image data with different (for example orthogonal) polarizations, in combination with polarization glasses. Encoding the stereoscopic image data by color filtering and combining 3-D glasses with color filters is likewise preferred. However, the display means might also be a 3-D electronic visual display, for example a light-field monitor or the like. According to this preferred embodiment, the control unit is further configured to ascertain a time-resolved first OCT image with a first virtual shadow and a time-resolved second OCT image with a second virtual shadow on the basis of the time-resolved OCT signal and a stereo angle, and to stereoscopically display the first OCT image and the second OCT image on the display means. In this case, the stereo angle is decisive for the depth impression within the scope of the image visualization on the display means and corresponds in the case of a stereo camera to the angle between the optical axes of the individual cameras, and consequently depends on both the spacing of the cameras from one another and on the working distance of the cameras from the object (sample). Such a stereo angle forms a basis of the generation of the stereoscopic OCT images by calculation, allowing variable setting of the stereo angle. As a rule, a large stereo angle corresponds to strong depth perception (like when the human eye perceives close objects) and a small stereo angle generally corresponds to a low depth perception (like when the human eye perceives distant objects). Consequently, the system according to the present disclosure advantageously enables a display of the OCT images with a variable depth impression. Preferably, the stereo angle can be ascertained on the basis of a user input. Consequently, a user, for example a surgeon, can advantageously adjust a stereo angle on an individual basis, with the result that taking account of the user input when ascertaining the stereo angle can advantageously also account for subjective preferences.

In a further preferred embodiment of the system according to the present disclosure, the control unit is further configured to ascertain the stereo angle on the basis of optical parameters of the surgical-microscopic system. In this case, the optical parameters of the surgical-microscopic system are acquired or read in the form of metadata by the control unit of the system according to the present disclosure. Consequently, the control unit is advantageously always informed about variable and fixed optical parameters of the surgical-microscopic system. In this case, the fixed optical parameters preferably characterize components of the surgical-microscopic system, for example utilized lens elements, eyepieces or the like, and the variable optical parameters in this case preferably characterize adjustable variables, for example a field of view, a resolution, an inclination of the optical axis, and the like. Taking account of the optical parameters of the surgical-microscopic system advantageously allows a simultaneous display of OCT images and video image data with an optimal adaptation of the image data to one another and, likewise, a sequential display of OCT images and video image data with an optimal transition.

In a particularly preferred embodiment of the system according to the present disclosure, the surgical-microscopic system comprises a stereo camera with a first stereo lens (in combination with a first image sensor) which is arranged along a first optical axis and designed to acquire a first image signal of the field of view and with a second stereo lens (in combination with a second image sensor) which is arranged along a second optical axis and designed to acquire a second image signal of the field of view. The surgical-microscopic system is therefore designed to acquire stereoscopic time-resolved image signals. In this case, the first optical axis and the second optical axis of the surgical-microscopic system include an angle, with this angle between the optical axes, together with the working distance between the sample and the lenses, determining the stereo angle of the stereoscopic image acquisition in the surgical-microscopic system. According to this embodiment, the control unit is preferably designed to determine the stereo angle which forms the basis of the ascertainment of the first OCT image and second OCT image and which corresponds to the stereo angle of the surgical-microscopic system. Further, the control unit is preferably designed to determine first video image data on the basis of the first image signal and second video image data on the basis of the second image signal. Consequently, this embodiment advantageously enables a stereoscopic display of both the video image data and the OCT images with corresponding stereo angle. This advantageously allows a stereoscopic simultaneous display with minimal deviations and a stereoscopic sequential display with an optimal transition between the various image modes (video and OCT image data). According to this embodiment, the optical parameters of the surgical-microscopic system are or comprise at least the parameters of the surgical-microscopic system which influence a stereo angle of same.

In a further preferred embodiment of the system according to the present disclosure, the control unit is configured to ascertain a phase of a performed operation and to ascertain the type, position, and/or alignment of the virtual light source on the basis of the phase of the performed operation. To this end, the control unit is preferably connected to a memory, in which a trained machine learning algorithm, for example a neural network (CNN) or the like, is stored. This algorithm was preferably trained by means of a multiplicity of video image data and/or OCT images or image signals and/or OCT signals, which were assigned a corresponding phase of an operation as a classification during the training. Accordingly, the trained algorithm is able to independently recognize a phase of an operation as a classification on the basis of video image data and/or OCT images or image signals and/or OCT signals. Preferably, the control unit according to this embodiment is designed to select a type, position, and/or alignment of the virtual light source corresponding to the ascertained phase of the operation. The types, positions, and/or alignments of the virtual light source suitable for different phases of the operation are preferably stored in a lookup table (LUT) in a memory or are likewise ascertained using a machine learning algorithm. By way of example, the latter can be trained by virtue of a multiplicity of video image data and/or OCT images or image signals and/or OCT signals having been assigned a corresponding phase of an operation and/or a corresponding stereo angle as one or more classifications during the training.

In the case of a cataract operation, the operation phases may for example comprise: rest state, incision, injection of the ophthalmic viscosurgical device (OVD), capsulorhexis, hydrodissection, phacoemulsification, rinse/aspiration, implantation of the intraocular lens, close/moisturize the wound, non-operation. In the case of a refractive operation, the operation phases may for example comprise: idling, docking, applanation, application of the eye/CG rotation, lens cut, lens side cut, flap cut, flap side cut, uncover the eye, transition to the surgical microscope, positioning of the surgical microscope, open the incision, define the planes, sever the flap bed, sever the lens bed, remove and/or inspect the lenses, wipe, rinse, slit lamp, remove the speculum. In the case of a dental intervention, the surgical phases may for example comprise: access, extirpation, debridement, drying, obturation, restoration. It should be noted that all or only some of these phases may be part of the corresponding operation and that further operation phases may also be present and/or some phases may be omitted.

The functionalities of the control unit according to the invention can be implemented by electrical or electronic devices or components (hardware), by firmware (ASIC) and/or can be realized by carrying out a suitable program (software). Preferably, the functionalities of the control unit according to the invention are realized or implemented by a combination of hardware, firmware and/or software. By way of example, individual components of the control unit according to the invention for carrying out individual functionalities are in the form of a separately integrated circuit or are arranged on a common integrated circuit.

The individual functionalities of the control unit according to the invention are further preferably in the form of one or more processes which run on one or more processors in one or more electronic computers and which are generated when carrying out one or more computer programs. In this case, the control unit is designed to cooperate with the other components, in particular the user interface, the OCT system, and the display means, in order to implement the functionalities of the system according to the invention as described herein. It is further evident to a person skilled in the art that the functionalities of a plurality of computers (data-processing devices, control units, controllers) can be combined or can be combined in a single device, or that the functionality of a specific data-processing device may be available distributed over a multiplicity of devices in order to realize the functionalities of the control unit according to the invention. In this case, the devices may be arranged in centralized fashion or in decentralized fashion at different locations. In the case of a decentralized arrangement, suitable communications means are configured between the devices in order to transfer data between these devices, the data being required to carry out the respective steps or to provide the respective functions of the individual devices.

In a particularly preferred embodiment of the system according to the invention, the latter is integrated in a surgical microscope. In this case, the surgical microscope preferably comprises an OCT system as described hereinabove. Further preferably, the surgical microscope comprises, or is connected to, an interface for user input and a display means. Preferably, the surgical microscope further comprises a surgical-microscopic system as described hereinabove, wherein image sensor and optical unit are part of a camera, in particular a main observer camera or a surround camera of the surgical microscope. The control unit of the surgical microscope is preferably designed as a control unit of the system according to the invention and, in particular, is designed to carry out the method according to the invention, as described hereinbelow, on the basis of commands stored on a storage unit of the surgical microscope.

Within the scope of the present disclosure, a surgical microscope is understood to mean in the broadest sense a microscope suitable for use during an operation. The surgical microscope preferably comprises a mount which allows imaging of the operating region independently of head movements of the surgeon. Further preferably, the surgical microscope comprises at least one piece of equipment for dividing the observation beam path and at least two eyepieces. Alternatively, the surgical microscope is a pure "digiscope" without eyepieces. Likewise preferably, the surgical microscope comprises at least one imaging sensor. Further preferably, the surgical microscope comprises a main observer camera and a surround camera. The surgical microscope may comprise kinematic or robotic aids for carrying out surgical procedures. As an alternative, a surgical microscope may be referred to as a medical engineering microscope, a medically approved microscope or a medical microscope.

A further aspect of the present disclosure relates to a method for visualizing OCT signals. The latter includes the method step of receiving a time-resolved OCT signal of a selected field of view of a sample from an OCT system (as described hereinabove). In this case, the OCT signal includes a multiplicity of tuples, which each contain or represent a volume element of the sample and a scattering intensity corresponding to the volume element. The method further includes the step of ascertaining a time-resolved OCT image with at least one object-specific virtual shadow, with the virtual shadow being ascertained by a virtual irradiation of at least one object of the OCT image by means of at least one virtual light source and with the object-specific virtual shadow being ascertained on at least one area of the OCT image. The method according to the present disclosure finally includes the display of the time-resolved OCT image with the at least one virtual shadow on the display means. The method according to the present disclosure realizes the same advantages as the system according to the present disclosure, and, in this respect, reference is made to the explanations given above.

In a preferred implementation of the method according to the present disclosure, the said method further includes the step of ascertaining the at least one object by segmenting the OCT signal or by segmenting the OCT image, preferably in each case using (on the basis of) object-specific pieces of information relating to the at least one object and/or a user input. As an alternative or in addition, the method according to the present disclosure further preferably includes the step of ascertaining the at least one area by segmenting the OCT signal or by segmenting the OCT image, preferably in each case using (on the basis of) area-specific pieces of information relating to the at least one area and/or a user input. Consequently, virtual shadows of semantically segmented objects are advantageously generated on semantically segmented areas.

Further preferred implementations of the method according to the present disclosure correspond to further preferred embodiments of the system according to the present disclosure and realize the same advantages as the embodiments.

A further aspect of the present disclosure relates to a computer program comprising commands which, when executed by a control unit as described hereinabove, preferably of a surgical microscope as described hereinabove, cause the system or surgical microscope as described hereinabove to carry out the method according to the invention as described hereinabove. The computer program preferably comprises commands which, when executed by a control unit as described hereinabove, preferably of a surgical microscope, cause the system or surgical microscope as described hereinabove to carry out the method according to the invention, in accordance with one of the preferred implementations, as described hereinabove. In this case, the computer program according to the invention is preferably stored in a volatile memory, for example a RAM element, or in a non-volatile storage medium, for example a CD-ROM, a flash memory or the like.

Further preferred embodiments of the invention will become clear from the other features set out in the dependent claims and from the figures explained below. The various embodiments of the invention that are set forth in this application can advantageously be combined with one another, unless specifically stated otherwise.

DESCRIPTION OF THE FIGURES

The invention will be explained below in exemplary embodiments with reference to the associated drawings, in which:

FIG. 1 shows a schematic illustration of a system 100 for acquiring and visualizing OCT signals 19 according to a first embodiment.

Figure 1:
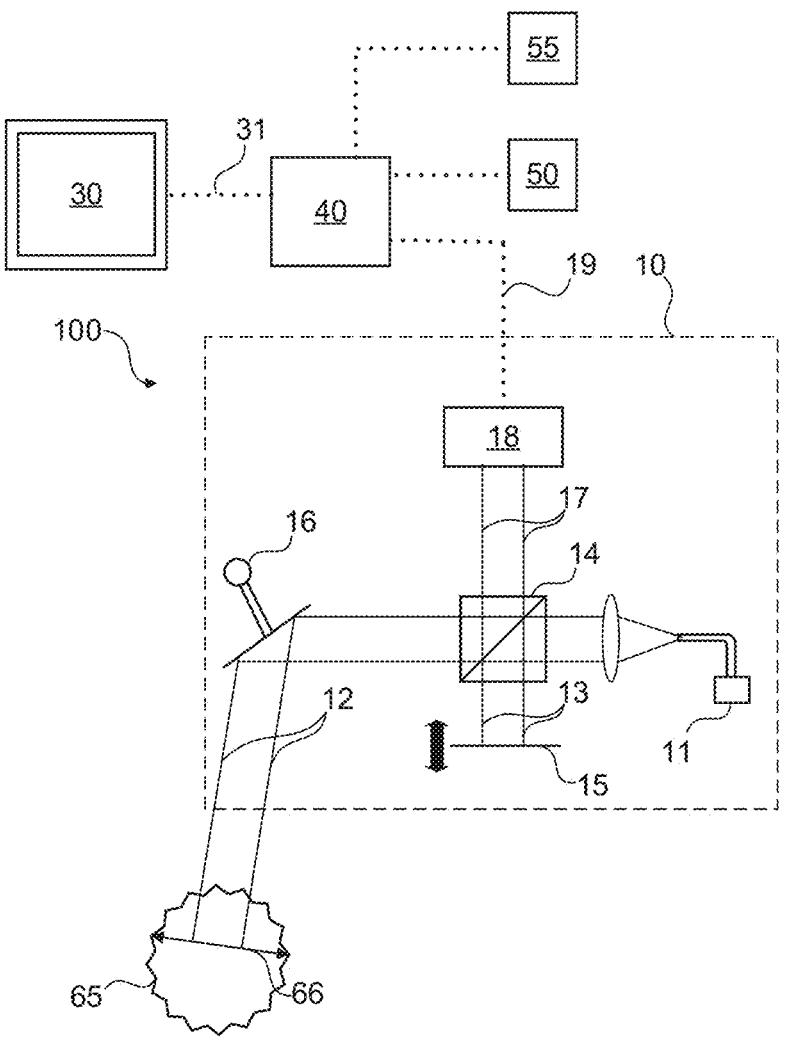
FIG. 1 shows a schematic illustration of a system for visualizing OCT signals according to a first embodiment.

The system 100 comprises an OCT system 10 having a broadband light source 11, for example a superluminescent diode. The light from the light source 11 is guided into an interferometer comprising a beam splitter 14 and a movable mirror 15. The light is split into a sample beam 12 and a reference beam 13 in the beam splitter 14. The sample beam 12 is scanned over the sample 65 by means of a scanning mirror 16, with at least one portion of a chosen field of view 66 of the sample 65 being scanned. The reference beam 13 is steered to the movable mirror 15 and reflected thereby back to the beam splitter 14. The sample beam 12 interacts with the sample 65, in particular with the volume of the sample 65, and is scattered back thereby to the scanning mirror 16, which steers the beam to the beam splitter 14. The back-scattered sample beam 12 and the reflected reference beam 13 are superimposed there, with a path difference between the superimposed beams 12, 13 being set by the movable mirror 15. The interference pattern 17 generated thus is acquired by means of a detector 18, for example a CCD detector or a CMOS detector.

The time-resolved OCT signal 19 acquired thus is transmitted from the detector 18 to the control unit 40. The control unit 40 is further connected to a user interface 50 for acquiring a user input and to a device interface 55 for receiving a device parameter. For example, the device interface 55 serves to receive a device parameter of a device connected to the device interface 55, for example of a surgical-microscopic system 20, of any other imaging system, or of a medical instrument 70. Further, the device parameter may originate from a tracking system (not depicted here) connected to the device interface 55 but characterize the medical instrument 70, for example its spatial pose.

For the acquired time-resolved OCT signal 19, the control unit 40 ascertains a time-resolved OCT image 31 with at least one virtual shadow 60 and transmits the time-resolved OCT image 31 with the virtual shadow 60 to the display means 30 for display purposes. Regarding explanations in relation to the virtual shadow 60, reference is made to the description hereinbelow, in particular of FIGS. 3 to 5.

Figure 2:
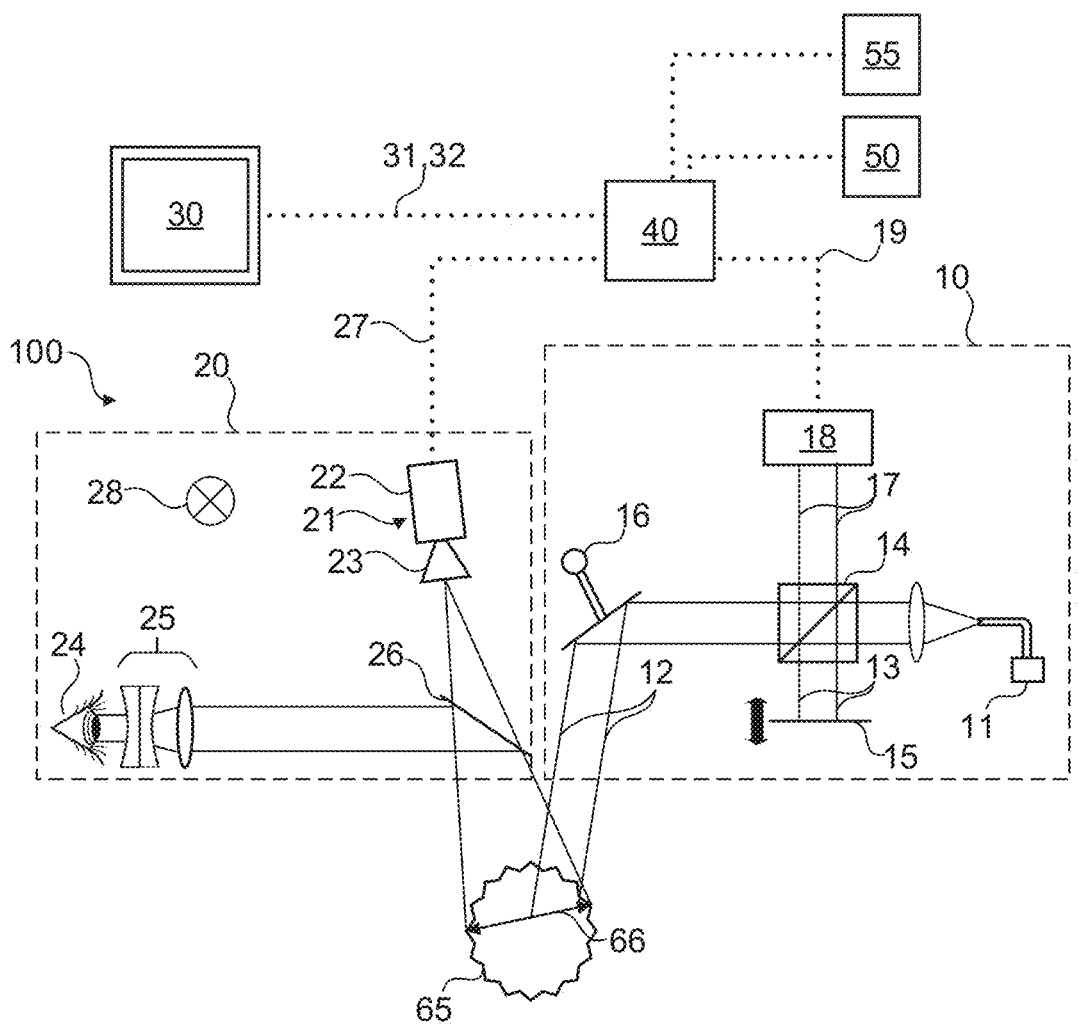
FIG. 2 shows a schematic illustration of a system for visualizing OCT signals according to a second embodiment.

FIG. 2 shows a schematic illustration of a system 100 for acquiring and visualizing OCT signals 19 according to a second embodiment. The same components are denoted by the same reference signs as in FIG. 1 and a repeated description of these components is therefore omitted.

The system 100 in FIG. 2 differs from that in FIG. 1 in that it further comprises a surgical-microscopic system 20 with a camera 21. The camera 21 comprises an image sensor 22 and an optical unit 23 and is designed to acquire the field of view 66 of the sample 65 such that a time-resolved image signal 27 is acquired as a result. The camera 21 can be a mono camera or a stereo camera. The sample 65 is illuminated by means of a real light source 28. For the acquired time-resolved image signal 27, the control unit 40 ascertains corresponding video image data 32, the video image data optionally containing a real shadow 64. In the system 100 of FIG. 2, a time-resolved OCT signal 17 is acquired in the same manner, and an OCT image 31 with a virtual shadow 60 is ascertained therefrom, as has already been described with reference to FIG. 1. The video image data 32 are displayed simultaneously or sequentially on the display means 30 together with the OCT images 31, wherein a change between the OCT images 31 and the video image data 32 is implemented on the basis of a user input acquired by means of the user interface 50, for example. Regarding explanations in relation to the display of a virtual shadow 60 in the OCT image 31 displayed simultaneously with the video image data 31, reference is made to the subsequent description of FIG. 6. The surgical-microscopic system 20 further comprises a piece of equipment for splitting the observation beam path 26, which splits the light beam transmitted from the field of view 66 of the sample 65 to the camera 23 and provides a component beam to the eye 24 of an observer via an eyepiece 25.

Figures 3, 4:
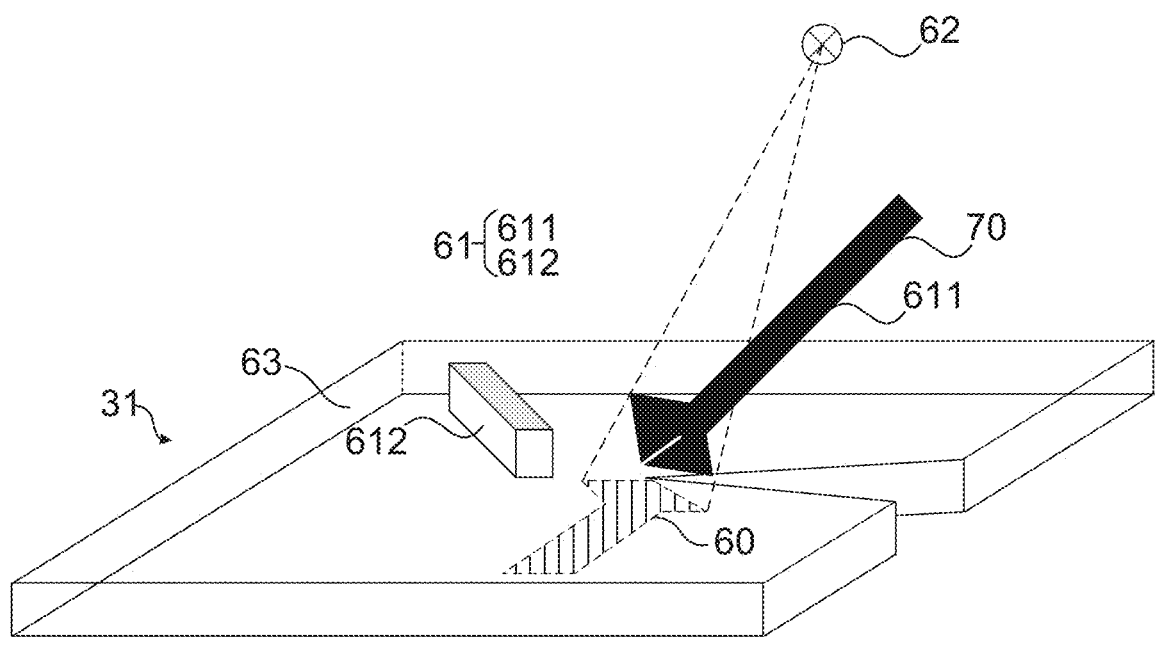
FIG. 3 shows a schematic illustration of the visualization of an OCT image with one object-related virtual shadow.
FIG. 4 shows a schematic illustration of the visualization of an OCT image with two object-related virtual shadows.

FIG. 3 shows a schematic illustration of the visualization of an OCT image 31 with one object-related virtual shadow 60. As described, the OCT image 31 is ascertained from the OCT signal 19 acquired from the field of view 66 of the sample 65, wherein a medical instrument 70 was in the vicinity of the sample 65 while the signal was acquired. The OCT image 31 comprises an image representation of an area 63 of the field of view 66 of the sample 65, an image representation of the medical instrument 70 as first object 611, and an image representation of an anatomical structure in the field of view 66 of the sample 65 as a second object 612. The scanning mirror 16 is used to steer the light from the broadband light source 11 of the OCT system 10 to the sample 65 in such a way that the light beams are incident virtually parallel to one another and at right angles to the sample surface in the field of view 66. The medical instrument 70 is manufactured from a material that is opaque to the radiation of the broadband light source 11. Consequently, the radiation of the broadband light source 11 does not reach a region below the medical instrument 70, with the result that the image representation of the area 63 below the medical instrument 70 is incomplete. In FIG. 3, this is represented by a triangular portion in the area 63 in which no OCT signal corresponding to the area 63 was acquired but only the signal corresponding to the medical instrument 70. Consequently, no OCT image 61 of the area 63 is available in this region. Consequently, this represents shadowing by the medical instrument 70. The prior art has disclosed methods that use a time series of OCT images, some of which contain the missing portion of the area 63 (for example because they were recorded prior to the approach of the medical instrument), to replace the missing part of the area 63 in an OCT image by combining pieces of image information from different OCT images in the time series.

The OCT image 31 further contains a virtual shadow 60. The latter was calculated as a shadow of the shadow-providing first object 611 when illuminated by the virtual light source 62 and was calculated on the area 63. In particular, the virtual shadow 60 was ascertained by ray tracing, wherein, upon incidence of a camera ray coming from a virtual camera (from a virtual observation direction) at a point of the area 63, a shadow ray is emitted from this point in the direction of the virtual light source 62, and a shadow is generated on the point of the area 63 if the shadow ray crosses the shadow-providing object 611 on its path to the virtual light source 62. Consequently, the virtual shadow 60 is generated in object-specific fashion for the medical instrument 70 since only a point of intersection between a shadow ray and the shadow-providing object 611 leads to a shadow on the area 63. In particular, a point of intersection between a shadow ray and the second object 612 does not lead to a shadow on the area 63, with the result that the anatomical structure of the second object 612 does not have a shadow in the OCT image 31. Moreover, the virtual shadow 60 is generated in area-specific fashion on the area 63 since a shadow ray is emitted thereby only upon incidence of a camera ray. In FIG. 3, shadow rays are depicted schematically using dashed lines.

FIG. 4 shows a schematic illustration of the visualization of an OCT image 31 with two object-related virtual shadows 601, 602. The OCT image 31 has been ascertained again from the OCT signal 19 generated from the field of view 66 of the sample 65, but has in this example a first area 631 and a second area 632 arranged below (subcutaneously to) the first area 631. FIG. 4 therefore reflects the advantageous properties of OCT images 31 which enable the three-dimensional and perspective illustration of slice or volume images of anatomical samples 65. In the OCT image 31 of FIG. 4, both the medical instrument 70 as first object 611 and the anatomical structure of the sample 65 as second object have a respective object-specific virtual shadow 60. In this case, the first virtual shadow 601 of the first object 611 is generated by virtual illumination of the first object 611 by the virtual light source 62 and, deviating from FIG. 3, generated on the subcutaneous area 632. The second virtual shadow 602 of the second object 612 is generated by virtual illumination of the second object 612 by the virtual light source 62 and generated on the top area 631. Once again, the virtual shadows 60 were generated by means of ray tracing, wherein arbitrary points in both areas 631 and 632 emit a shadow ray (depicted using dashed lines) to the virtual light source 62 when struck by a camera ray (not depicted here) in this example. In this case, however, a virtual shadow 601 is only generated on a point in the area 631 if the shadow ray crosses the first object 611 on the path to the virtual light source 62 and a virtual shadow 602 is only generated on a point in the area 632 if the shadow ray crosses the second object 612 on the path to the virtual light source 62. Consequently, the virtual shadows 601, 602 in each case are generated in object-specific fashion only for specific shadow-providing objects 611, 612 and in area-specific fashion only on specific shadow-receiving areas 631, 632. Consequently, each of the virtual shadows 601, 602 is uniquely assignable to a combination of object and area.

Figure 5:
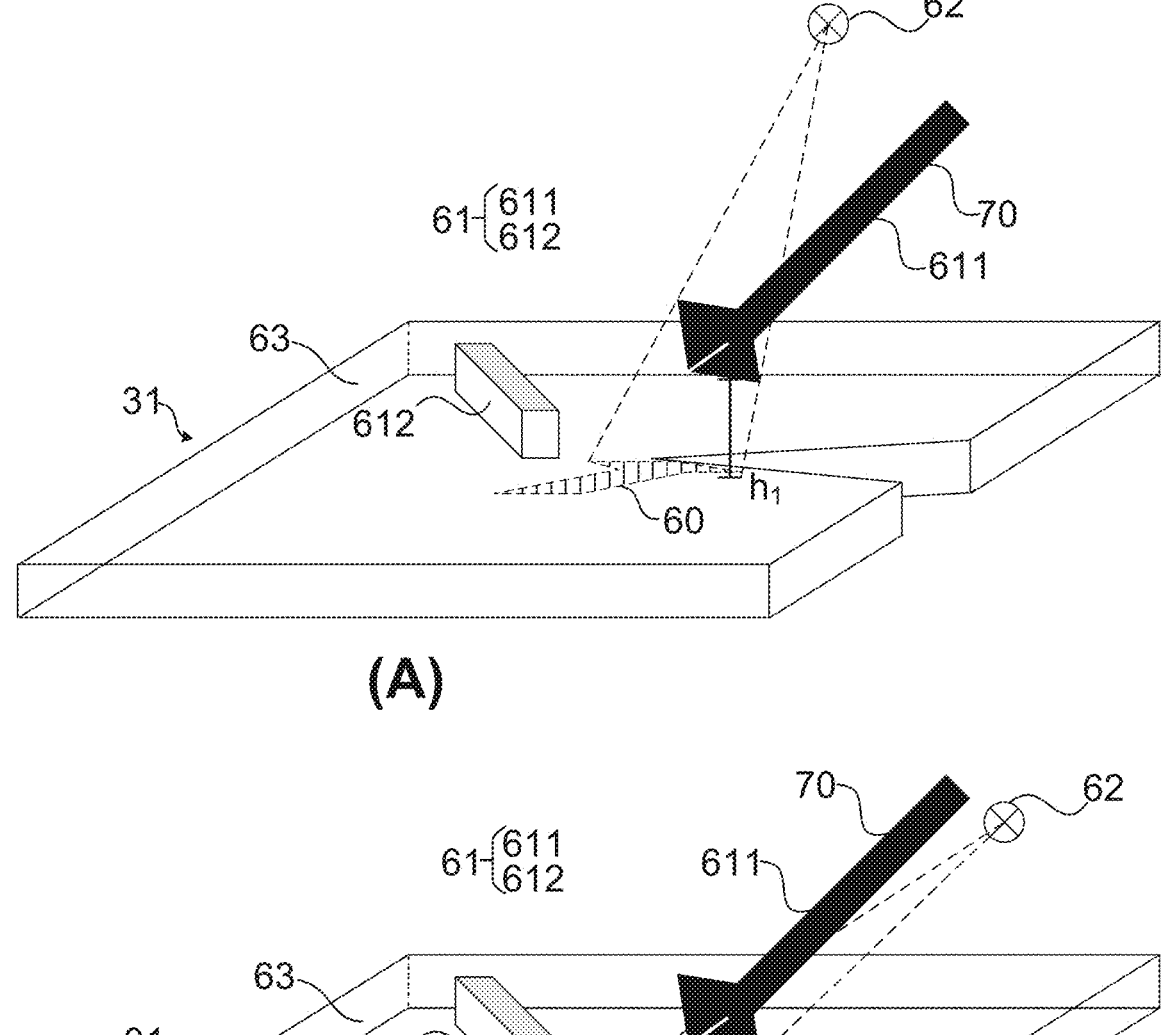
FIG. 5 shows a schematic illustration of the visualization of an OCT image with (A) a first object-related virtual shadow and (B) a second object-related virtual shadow.

As a result of the virtual shadows 60 in the OCT images 31, these are better interpretable by a user, especially with regards to the relative pose of objects 61 and areas 63 in the OCT image 31. In this respect, FIG. 5 shows a schematic illustration of the visualization of an OCT image with (A) a first object-related virtual shadow and (B) a second object-related virtual shadow. Here, the basic situation in FIG. 5 corresponds to the situation in FIG. 3; thus, a virtual shadow 60 is generated only by the medical instrument 70 as first object 611 and generated only on the area 63 while, by contrast, a virtual shadow of the second object 612 is not generated. In the image representation of FIG. 5(A), the medical instrument 70 is situated at a first distance $h_1$ above the area 63 and the virtual light source 62 is situated at a first position. In the image representation of FIG. 5(B), the medical instrument 70 is situated at a second distance $h_2$ above the area 63 and the virtual light source 62 is situated at a second position. In this case, the second distance $h_2$ is shorter than the first distance $h_1$ and the second position of the virtual light source 62 has a shorter perpendicular distance from the area 63 than the first position of the virtual light source 62.

Hence, the virtual shadow 60 of the first object 611 in FIG. 5(A) is shorter than the virtual shadow of the first object 611 in FIG. 5(B) and relative changes in pose of the medical instrument 70 can be identified better on the basis of the virtual shadow 60, the closer the medical instrument 70 is brought to the area 63 (for example a retina in an ophthalmological procedure). For example, a user can derive a distance between the tip of the medical instrument 70 and the area 63 on the basis of the distance between the tip of the medical instrument 70 and the corresponding tip of the virtual shadow 60. If the tip of the medical instrument 70 is in contact with the area 63, then this distance is zero. By reducing the perpendicular distance between virtual light source 62 and area 63 when the medical instrument 70 comes closer to the area 63, the virtual shadow 60 is scaled longer, allowing finer control of the medical instrument 70 on the basis of the virtual shadow 60. In the example of FIG. 5, the virtual light source 62 is preferably depicted in the OCT image 31 such that a user can identify a movement of the virtual light source 62. Likewise preferably, the position of the virtual light source 62 remains constant when a predetermined distance between medical instrument 70 and area 63 is undershot, with the result that any change in the virtual shadow 60 is caused solely by the movement of the instrument 70.

Figure 6:
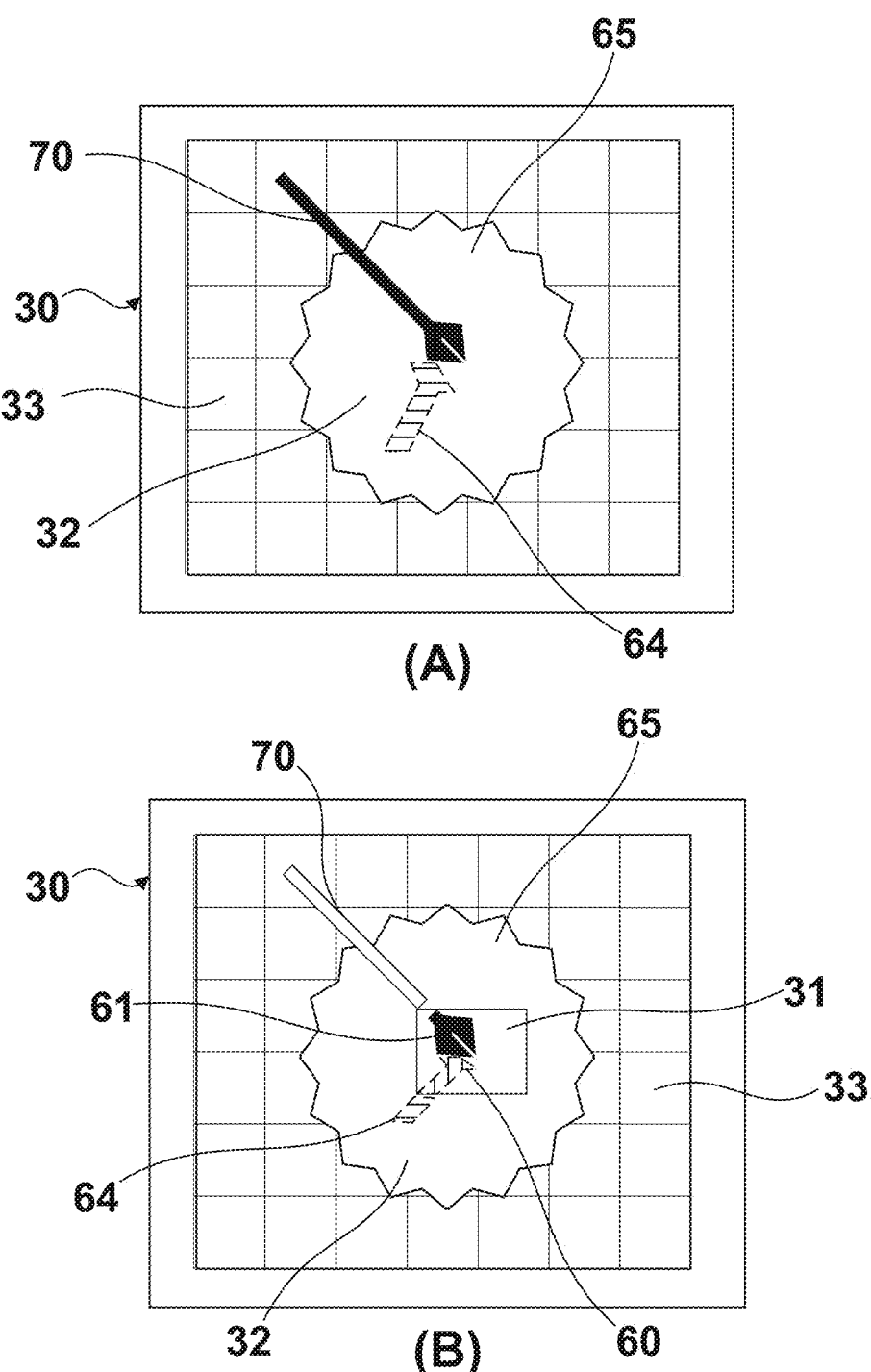
FIG. 6 shows a schematic illustration of the visualization (A) of a video image with a shadow and (B) an OCT image with an object-related virtual shadow and a video image with a shadow.

FIG. 6 relates to the multimodal display of OCT images 31 and video image data 32 on the display means 30, as already explained with reference to FIG. 2. Here, FIG. 6(A) shows a schematic illustration of the visualization of a video image 32 with a shadow 64, and FIG. 6(B) shows a schematic illustration of the visualization of an OCT image 31 with an object-related virtual shadow 60 and of a video image 32 with a shadow 64.

Here, FIG. 6(A) for example illustrates a first phase of an ophthalmological procedure, in which a medical instrument 70 is brought to a sample 65, for example to an eye of a patient. A video image 32 is sufficient for the surgeon to this end since the instrument 70 does not yet engage with the sample 65. Here, this video image 32 is displayed on the pixels of the display means 30 and contains an image representation of the sample 65, of the medical instrument 70, and of a real shadow 64. In this case, the real shadow 64 is generated by illuminating the medical instrument 70 by means of the real light source 28 in FIG. 2 and generated without difference on all areas of the sample 65 otherwise irradiated by the real light source 28. FIG. 6(B) illustrates a second phase of the ophthalmological intervention, which is initiated for example by a user input or automatically when a predetermined distance between medical instrument 70 and sample 65 is undershot. In the second phase, an OCT image 31 of a defined region (region of interest—ROI) of the sample 65 is depicted on the pixels 33 of the display means 30, in a manner overlaid on the video image data 32 of the remaining sample 65. In this case, the OCT image 31 contains a front portion (depicted filled in black) of the medical instrument 70, whereas the remainder (as depicted) of the medical instrument 70 is visible in the video image data 32. Further, the video image data 32 also depict a portion of the real shadow 64, and the OCT image contains a virtual shadow 60 which merges seamlessly into the real shadow 64. In this case, the virtual shadow 60 is generated by a virtual illumination of the image representation of the medical instrument 70 in the OCT image 31 by means of a virtual light source 31 that is arranged at the position of the real light source 64. This consequently prevents confusing the user by deviating shadow profiles and ensures a seamless transition between the display modes of FIG. 6(A) and FIG. 6(B).

Figure 7:
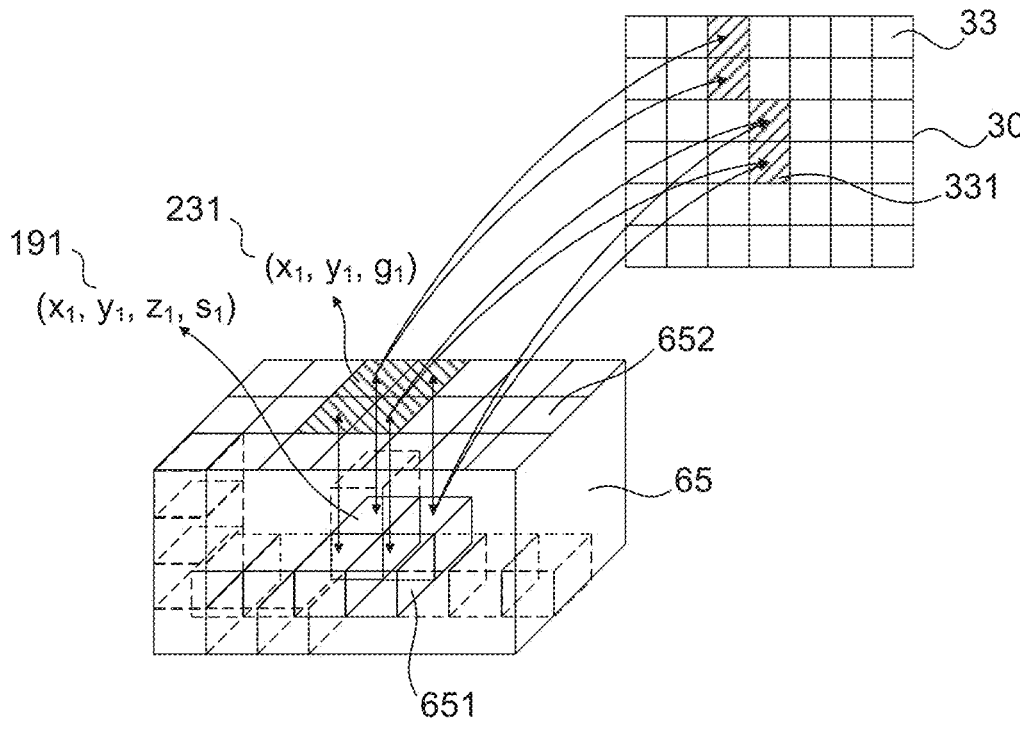
FIG. 7 shows a schematic illustration of a sample and a display means according to an embodiment.

FIG. 7 shows a schematic illustration of a sample 65 and a display means 30 according to an embodiment. In this case, the sample 65 comprises a multiplicity of volume elements 651 and a multiplicity of surface elements 652, with specific volume elements 651 corresponding to specific surface elements 652. An exemplary selection of surface elements 652 is depicted with hatching and four volume elements 651 corresponding to the hatched surface elements 652 are depicted using solid lines, while the remaining volume elements 651 are depicted using dashed lines. Further, double-headed arrows connect these volume elements 651 to the associated surface elements 652.

The OCT system 10 of the system 100 of FIGS. 1 and 2 in particular renders the volume of the sample 65 acquirable, by virtue of short-wavelength light of the sample beam 12, scattered thereby, being superimposed via the scanning mirror 16 on the reference beam 17 by means of the interferometer. The interference pattern 17 created thus, acquired by means of the detector 18 as a time-resolved OCT signal 19, includes a multiplicity of first tuples 191, with a number of the first tuples 191 for example arising from a number of the points on the sample 65 scanned by means of the scanning mirror 16. In this case, each of the first tuples 191 corresponds to one of the displayed volume elements 651 and contains a value of a scattering intensity $s_i$. Further, each of the first tuples 191 is assigned three spatial coordinates $x_i$, $y_i$, $z_i$ on the basis of a calibration or registration of the OCT system 10 relative to a coordinate system of the sample 65 (patient). In the illustrated example, a first tuple 191 contains the spatial coordinates $x_1$, $y_1$, $z_1$ and the scattering intensity value $s_1$.

The surface of the sample 65, in particular, is capturable using the surgical-microscopic system 20 of the system 100 of FIG. 2 by virtue of long-wavelength (visible) light reflected or scattered back from said surface being cast back to the image sensor 22 of the camera 21 via the optical units 23. The image signals 27 acquired by means of the image sensor 22 then each include a multiplicity of second tuples 231, with a number of the second tuples 231 arising from a resolution of the image sensor 22. Here, each of the second tuples 231 corresponds to one of the displayed surface elements 652 and contains a grayscale value $g_i$ corresponding to an intensity of the light cast back to the image sensor 22. Further, each of the second tuples 231 is assigned two lateral spatial coordinates $x_i$, $y_i$ on the basis of a calibration or registration of the image sensor 22 relative to a coordinate system of the sample 65 (patient). In the illustrated example, a second tuple 231 contains the lateral spatial coordinates $x_1$, $y_1$ and the grayscale value $g_1$.

The display means 30 further depicted in FIG. 7 comprises a multiplicity of pixels 33, in particular 42 pixels, with 7 pixels in the horizontal direction and 6 pixels in the vertical direction. In the illustrated example, the resolution of the image sensor 22 yielded an acquisition of the sample surface by the image signals 27 in 21 surface elements 652 with 7 surface elements 652 in the horizontal direction and 3 surface elements 652 in the vertical direction. Thus, in the video image data 32, one pixel 33 corresponds to one surface element 652 in the horizontal direction, and two pixels 33 correspond to one surface element 652 in the vertical direction. Pixels 33 corresponding to surface elements 652 depicted with hatching are likewise depicted with hatching and the assignment is further elucidated by arrows. As further depicted by arrows, the control unit 40 of the system 100 also generates the associated OCT image 31 of the volume elements 651 corresponding to the surface elements 652 and depicts the said OCT image in the respective pixels 33 so that video image data 32 of certain surface elements 652 are depicted on specific pixels 33 and OCT images 31 of volume elements 651 corresponding to the surface elements 652 are likewise depicted on the specific pixels 33. Consequently, corresponding OCT images 31 and video image data 32 are depicted at the same location of the display means 30, and a virtual shadow calculated on a specific volume element 651 (with reference sign) is depicted on the corresponding pixel 331. Thus, a correct assignment of the virtual shadows to the corresponding pixels 33 is ensured.

Figure 8:
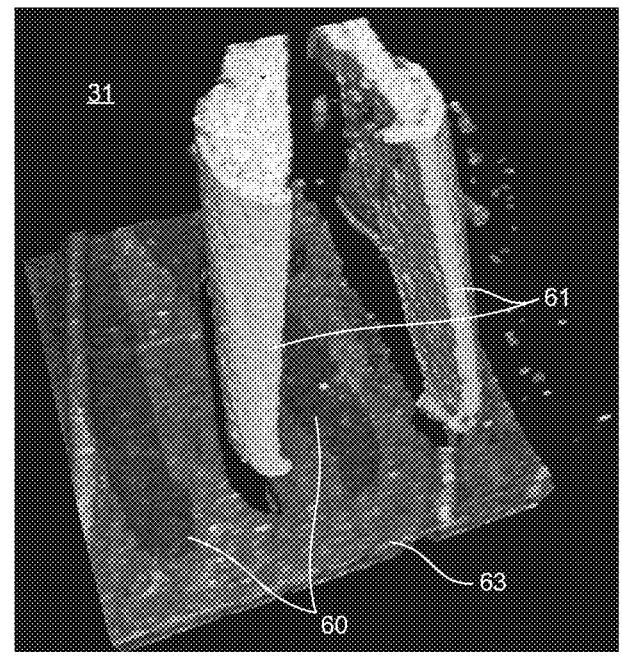
FIG. 8 shows an illustration of a visualized OCT image with one object-related virtual shadow.

FIG. 8 shows an illustration of a visualized OCT image 31 with an object-related virtual shadow 60, in particular an object-related virtual shadow 60 of the tips 61 of surgical tweezers as shadow-providing object 61 on a retinal layer 63. In this case, the retinal surface layer (ILM) 63 was segmented in the real-time volume calculation from OCT B-scans using a conventional image processing approach (threshold value-based). The surgical tweezer tips 61 are initially segmented by segmenting a 2-D plan view of the volume, wherein there is an identification for each A-scan as to whether the latter contains an image representation of the tweezer tips 61. On account of the attenuation of the OCT signal 19 at the instrument surface, only the instrument 61 can be found in the OCT images of these A-scans, which is why the 3-D position of the instrument 61 can be ascertained on the basis of threshold values in slice images (B-scans) associated with the identified A-scans. Alternatively, the positions of the retinal layer 63 and instrument 61 may also be ascertained (segmented) directly in the B-scans with the aid of a machine learning algorithm, for example a neural network.

Figure 9:
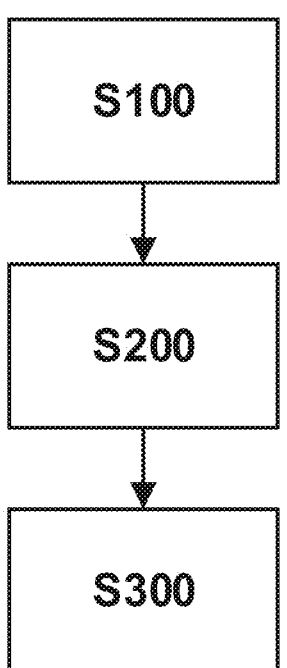
FIG. 9 shows a schematic flowchart of a method according to an implementation.

FIG. 9 shows a schematic flowchart of a method according to an implementation. The method includes a first step S100 of receiving a time-resolved OCT signal 19 of a selected field of view 66 of a sample 65 from an OCT system 10. In this case, the OCT signal 19 includes a multiplicity of tuples 191, which each represent a volume element 651 of the sample 65 and a scattering intensity corresponding to the volume element 651. The method further includes the second step S200 of ascertaining S200 a time-resolved OCT image 31 with an object-specific virtual shadow 60 by a virtual irradiation of at least one object 61 of the OCT image 31 by means of a virtual light source 62 on at least one area 63 of the OCT image 31. Finally, the time-resolved OCT image 31 is displayed with the virtual shadow 60 on the display means 30 in a third step S300.

The invention claimed is:

1. A system for visualizing OCT signals, comprising:
a display means designed for the time-resolved display of image data; and
a control unit, which is configured
    to receive a time-resolved OCT signal of a selected field of view of a sample from an OCT system;
    to ascertain a time-resolved OCT image with at least one virtual shadow on the basis of the OCT signal, with at least one shadow-generating object of interest and at least one shadow-receiving area of interest being ascertained on the basis of the OCT signal or OCT image,
    with the at least one virtual shadow being generated in object-specific fashion on the at least one shadow-receiving area of the OCT image by a virtual irradiation of the at least one shadow-generating object of the OCT image by means of a virtual light source; and
    to display the time-resolved OCT image on the display means,
    with the control unit being further configured
        to ascertain the at least one shadow-generating object of interest and/or the at least one shadow-receiving area of interest by way of a targeted segmentation of the OCT signal or OCT image, or
        to segment a multiplicity of objects and/or areas in the OCT signal or OCT image and select the at least one shadow-generating object of interest and/or the at least one shadow-receiving area of interest therefrom.

2. The system as claimed in claim 1, wherein the control unit is configured to ascertain the at least one shadow-generating object on the basis of object-specific pieces of information and/or the at least one shadow-receiving area on the basis of area-specific pieces of information.

3. The system as claimed in claim 1, wherein the system further comprises an interface designed to acquire a user input, with the selection of the at least one shadow-generating object of interest and/or of the at least one shadow-receiving area of interest being implemented on the basis of the user input.

4. The system as claimed in claim 1, wherein the control unit is configured to ascertain the OCT image as a 3-D volume image from the OCT signal by means of volume rendering, ray tracing and/or ray marching.

5. The system as claimed in claim 1, wherein the control unit is configured to vary the position, alignment, and/or type of the virtual light source and/or display this in the time-resolved OCT image.

6. The system as claimed in claim 5, wherein the system further comprises an interface designed to acquire a user input and the control unit is configured to set the position, alignment, and/or type of the virtual light source on the basis of the user input, and/or wherein the system further comprises a device interface designed to acquire a device parameter and the control unit is configured to set the position, alignment, and/or type of the virtual light source on the basis of the device parameter.

7. The system as claimed in claim 5, further comprising a medical instrument, wherein the control unit is configured to ascertain a position, a type, and/or a state of the medical instrument and to ascertain the position, alignment, and/or type of the virtual light source on the basis of the position, the type, and/or the state of the medical instrument.

8. The system as claimed in claim 1, wherein the control unit is configured to display the virtual shadow with a color code in the time-resolved OCT image.

9. The system as claimed in claim 1, wherein the OCT signal includes a multiplicity of tuples each representing a volume element of the sample and a scattering intensity, wherein the display means comprises a multiplicity of pixels and wherein the control unit is configured to ascertain OCT images in such a way on the basis of the tuples and a resolution of the display means that specific pixels correspond to specific volume elements, and to represent a virtual shadow ascertained on specific volume elements on the corresponding pixels.

10. The system as claimed in claim 1, further comprising:
a surgical-microscopic system comprising a real light source and being designed to acquire a time-resolved image signal of the selected field of view of the sample, wherein the control unit is further configured to ascertain corresponding video image data on the basis of the acquired time-resolved image signal, to simultaneously or sequentially display the video image data and the time-resolved OCT image on the display means, and to generate the virtual shadow by means of a virtual light source corresponding to the real light source.

11. The system as claimed in claim 10, wherein the control unit is configured to sequentially display the video image data and the time-resolved OCT image on the display means with the same magnification, the same perspective, and/or the same stereo angle $\alpha$ or to simultaneously display the video image data with a first level of transparency and the time-resolved OCT image with a second level of transparency on the display means.

12. A method for visualizing OCT signals, including the method steps of:
receiving a time-resolved OCT signal of a selected field of view of a sample from an OCT system, with the OCT signal including a multiplicity of tuples each representing a volume element of the sample and a scattering intensity corresponding to the volume element;
ascertaining a time-resolved OCT image with at least one object-specific virtual shadow, with at least one shadow-generating object of interest and at least one shadow-receiving area of interest being ascertained on the basis of the OCT signal or OCT image and with the at least one object-specific virtual shadow being generated on the at least one shadow-receiving area of the OCT image by a virtual irradiation of the at least one shadow-generating object of the OCT image by means of a virtual light source; and
displaying the time-resolved OCT image on the display means,
with the at least one shadow-generating object of interest and/or the at least one shadow-receiving area of interest being ascertained by way of a targeted segmentation of the OCT signal or OCT image, or
with a multiplicity of objects and/or areas in the OCT signal or OCT image being segmented and the at least one shadow-generating object of interest and/or the at least one shadow-receiving area of interest being selected therefrom.

13. The method as claimed in claim 12, including the method steps of:
ascertaining the at least one shadow-generating object by a segmentation of the OCT signal or OCT image and preferably on the basis of object-specific pieces of information and/or a user input; and/or
ascertaining the at least one shadow-receiving area by a segmentation of the OCT signal or OCT image and preferably on the basis of area-specific pieces of information and/or a user input.

14. A non-transitory computer-readable storage medium storing computer-readable instructions which, upon execution by a control unit, cause a system to carry out a method as claimed in claim 12.

* * * * *